US00PP37149P2

(12) United States Plant Patent
Lim

(10) Patent No.: US PP37,149 P2
(45) Date of Patent: Dec. 16, 2025

(54) FLORIBUNDA ROSE PLANT NAMED 'ALTtiger'

(50) Latin Name: *Rosa hybrida*
Varietal Denomination: ALTtiger

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,462

(22) Filed: Jan. 15, 2025

(51) Int. Cl.
*A01H 5/02* (2018.01)
*A01H 6/74* (2018.01)

(52) U.S. Cl.
USPC ..... Plt./143
CPC ..... *A01H 6/74* (2018.05)

(58) Field of Classification Search
USPC ..... Plt./143
CPC ..... A01H 5/0222
See application file for complete search history.

*Primary Examiner* — Kent L Bell

(57) ABSTRACT

A new and distinct cultivar of Rose plant named 'ALTtiger' is disclosed, characterized by distinctive yellow flowers with deep pink stripes. The new cultivar has a compact growth habit and can be grown commercially on its own roots. Plants have dark, foliage resistant to black spot and powdery mildew disease. The new variety is normally produced as an outdoor garden or container plant.

1 Drawing Sheet

Latin name of the genus and species: *Rosa hybrida.*
Variety denomination: 'ALTtiger'.

BACKGROUND OF THE INVENTION

The new *Rosa* cultivar is a product of a planned breeding program conducted by the inventor, Peter Ping Lim. The objective of the breeding program was to produce vigorous new garden rose varieties for ornamental commercial applications. The cross resulting in this new variety was made in Vista, California in May of 2016.

The seed parent is an unnamed, unpatented proprietary variety. The pollen parent is *Rosa* 'WEKgobnez' U.S. Plant Pat. No. 20,936. The new variety was selected in June of 2017 by the inventor in a group of seedlings resulting from the 2016 crossing, in a nursery Vista, California.

Asexual reproduction of the new cultivar has been performed by vegetative cuttings. This was first performed at a research greenhouse in Vista, California in June of 2017 and has shown that the unique features of this cultivar are stable and reproduced true to type in successive generations.

SUMMARY OF THE INVENTION

The cultivar 'ALTtiger' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTtiger'. These characteristics in combination distinguish 'ALTtiger' as a new and distinct *Rosa* cultivar:

1. Floribunda rose.
2. Yellow flowers with deep pink stripes.
3. Compact growth habit.

4. Plants can be grown on their own roots; grafting is not required.
5. Dark glossy foliage is resistant to black spot and powdery mildew diseases.

PARENT COMPARISONS

Plants of the new cultivar 'ALTtiger' are similar to plants of the seed parent, in most horticultural characteristics, however, plants of the new cultivar 'ALTtiger' differ in the following:

1. Flowers of the new cultivar have a deep pink stripe not found on the solid yellow flowers of the seed parent.

Plants of the new cultivar 'ALTtiger' are similar to plants of the pollen parent in most horticultural characteristics, however, plants of the new cultivar 'ALTtiger' differ in the following:

1. Flower color of the new cultivar is yellow with a deep pink stripe, while flower color of the pollen parent is ivory with red stripes.
2. Plants of the new cultivar are more compact than plants of the pollen parent.

COMMERCIAL COMPARISONS

Plants of the new cultivar 'ALTtiger' can be compared to the commercial variety *Rosa* 'George Burns', U.S. Plant Pat. No. 13,334. These varieties are similar in most horticultural characteristics, however 'ALTtiger' differs in the following:

1. Flowers color of the new cultivar is a brighter yellow and the stripes are pink compared to the dark burgundy stripe and soft yellow of this comparator.
2. Plants of the new cultivar are more compact than plants of this comparator.

Plants of the new cultivar 'ALTtiger' can also be compared to the commercial variety *Rosa* 'Claude Monet', unpatented. These varieties are similar in most horticultural characteristics, however 'ALTtiger' differs in the following:

1. Flowers of the new cultivar are smaller than flowers of this comparator.
2. Flowers of the new cultivar do not have as much pink on the petals as this comparator.
3. Plants of the new cultivar do not need to be grafted to grow vigorously; plants of this comparator require grafting for adequate vigor.

BRIEF DESCRIPTION OF THE PHOTOGRAPH

The accompanying photograph illustrates in full color a close up of an individual flower from a plant of about 18 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ALTtiger' plants grown outdoors, in Palm Desert, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTtiger'.

Market classification: Floribunda rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Compact.

Container size: 2-gallon.

Height: 48 cm.

Plant spread: 60 cm.

Rootstock: Own root.

Growth rate: Moderate.

Branching characteristics: Sympodial branching.

Length of primary lateral branches: Average range 22 to 42 cm.

Diameter of lateral branches: Approximately 5 mm to 6 mm.

Quantity branches: 6 to 8 main branches, moderate lateral branches, 5 to 8 lateral branches per main branch.

Branches:

*Young wood.*—

*Diameter.*—Approximately 4 mm.

*Texture.*—Glabrous, sparse minute, soft, short thorns.

*Approximately density/quantity of prickles.*—Sparse.

*Color.*—Near Green 143A.

Branches:

*Old wood.*—

*Diameter.*—Approximately 5 to 9 mm.

*Color.*—Near Yellow-Green 144A. Oldest section has longitudinal scales colored near Grey 201C.

*Texture.*—Glabrous. Oldest, basal growth very slightly scaly.

Thorns:

*Approximately density/quantity of thorns.*—Young growth: Sparse. Approximately 4 mm wide at base and 10 mm long. Weakly hooked. Colored near Greyed-Purple 183A. Mature growth: Moderately dense, apiculate thorns about 8 mm at base, 9 mm to 12 mm long. Colored near Greyed-Orange 174A. Not hooked.

FOLIAGE

Leaf:

*Arrangement.*—Alternate and compound.

*Quantity.*—Average 10 to 16 per main branch.

*Internode.*—Average 3.5 cm to 6.5 cm.

*Average length.*—Approximately 11 cm.

*Average width.*—Approximately 7 cm.

Rachis:

*Average length.*—Approximately 4 cm.

*Average diameter.*—Approximately 3 mm.

*Color.*—Upper surface: Near RHS Green 137A. Lower surface: Near RHS Green 143B.

*Texture.*—Upper Surface: Glabrous. Lower Surface: Glabrous with a single small sharp thorn at leaflet pair nodes. Thorn about 4 mm long, colored near RHS Yellow-Green 153A.

Leaflet:

*Quantity.*—7.

*Average length.*—Approximately 3 to 4 cm.

*Average width.*—Approximately 2.5 cm to 4.0 cm.

*Shape of blade.*—Broad ovate.

*Apex.*—Acute.

*Base.*—Broadly rounded.

*Margin.*—Very finely serrate.

*Appearance of top surface.*—Very glossy.

*Appearance of bottom surface.*—Matte.

*Texture of top surface.*—Glabrous.

*Texture of bottom surface.*—Glabrous.

*Color.*—Young foliage upper side: Near RHS Yellow-Green 144B. Young foliage under side: Near RHS Green 137B. Mature foliage upper side: Near RHS Green 139A. Mature foliage under side: Near RHS Green 137B.

*Venation.*—Type: Reticulate. Venation color upper side: Near RHS Green 143C. Venation color under side: Near RHS Yellow-Green N144C.

Petiole:

*Average length.*—Approximately 2.5 cm.

*Average diameter.*—Approximately 3 mm.

*Color.*—Upper surface: Near RHS Yellow-Green 144A. Lower surface: Near RHS Yellow-Green 144B.

*Petiole wing.*—Typically 11 mm long and 4 mm wide. Apex apiculate. Upper surface colored near RHS Yellow-Green 144A, lower surface colored near Yellow-Green 144B. Texture: Glabrous.

FLOWER

Natural flowering season: Spring until Autumn.

Inflorescence type and habit: Singly occurring fully double rotate flowers.

Rate of flower opening: Approximately 5 days from bud to fully opened flower.

Flower longevity on plant: About 1 week.

Quantity of flowers: 16 to 24 fully opened flowers and buds.

Flower shape:

*From above*.—Round.

*Profile of upper part of flower*.—Flat.

*Profile of lower part of flower*.—Nearly flat, lowest petals reflex down slightly.

Flower size:

*Diameter*.—Approximately 8 cm.

*Height*.—Approximately 4.8 cm.

Peduncle:

*Length*.—Average range 3.5 to 5 cm.

*Diameter*.—4 mm.

*Color*.—Near RHS Green 143B.

*Texture*.—Glabrous.

Petals:

*Petal arrangement*.—Multiple rotate, overlapping whorls.

*Petal quantity*.—Average 30.

*Length*.—Average 3.5 to 4 cm.

*Width*.—Average inner petals 2.2 cm; average outer petals 4.1 cm.

*Shape*.—Broad deltate.

*Margin*.—Entire, Strongly reflexed, rolled back with age.

*Apex*.—Rounded, 1 or 2 irregular notches.

*Base*.—Attenuate.

*Texture*.—Glabrous all surfaces.

*Color*.—When opening: Upper surface: Near RHS Yellow 12B. Irregular streaks and blotches covering between 10 to 30% of petal surface colored near Red 51A. Small basal blotch near Yellow-Orange 15A. Lower surface: Near RHS Yellow 9C. Irregular streaks and blotches covering between 10 to 20% of petal surface (mainly near margins and apex) colored near Red 51B. Basal blotch near Yellow 12A. Fully opened: Upper surface: Near RHS Yellow 8A. Irregular streaks and blotches covering between 10 to 30% of petal surface colored near Red 52A. Small basal blotch near Yellow-Orange 15A. Lower surface : Near RHS Yellow 9C. Irregular streaks and blotches covering between 10 to 20% of petal surface (mainly near margins and apex) colored near Red 51B. Basal blotch near Yellow 11A. Aging: Upper surface: Near RHS Yellow 8C and 8D. Irregular streaks and blotches covering between 10 to 30% of petal surface colored near Red 54C. Small basal blotch near Yellow 10A. Lower surface: Near RHS Yellow 8D. Irregular streaks and blotches covering between 10 to 20% of petal surface colored near Red 54C. Small basal blotch near Yellow 10A.

Bud:

*Shape*.—Ovate.

*Length*.—Approximately 3 cm.

*Diameter*.—Approximately 3 cm.

*Color*.—Near RHS Yellow 13C, small streaks near Red 53C.

Sepals:

*Quantity*.—5.

*Length*.—2.5 cm.

*Width*.—9 mm.

*Shape*.—Deltoid.

*Apex*.—Apiculate. Sepal extension absent.

*Margin*.—Entire.

*Texture*.—Upper Surface: Pubescent. Lower surface: Glabrous.

*Color*.—Interior Surface: Near RHS Green 138B. Exterior Surface: Near RHS Green 138A.

Receptacle:

*Height*.—6 mm.

*Width*.—9 mm.

*Shape*.—Flat.

*Color*.—Near RHS Yellow-Green 145C.

Fragrance: Moderate to strong floral/tea rose scent.

REPRODUCTIVE ORGANS

Stamens:

*Quantity*.—About 40.

*Filament length*.—Approximately 11 mm.

*Filament color*.—Near RHS Yellow 6D.

Anthers:

*Length*.—3 mm.

*Shape*.—Narrow globular.

*Color*.—Near RHS Yellow 13A.

*Pollen*.—Color: Near RHS Yellow-Orange 17B. Quantity: Scant.

Pistil: Misshapen, globular structure in center of the flower. About 4 mm in length and 5 mm wide. Colored near Yellow-Green 153D.

OTHER CHARACTERISTICS

Seeds and fruits: Not observed.

Disease/pest resistance: Good overall resistance to normal pests of garden roses. Resistant to blackspot (*Diplocarpon rosae*) and powdery mildew (*Podosphaera pannosa*) diseases. In a three-year confidential field trial of garden roses the new variety 'ALTtiger' remains free of powdery mildew year-round while varieties planted nearby showed symptoms of powdery mildew.

What is claimed is:

1. A new and distinct cultivar of Rose plant named 'ALTtiger' as herein illustrated and described.

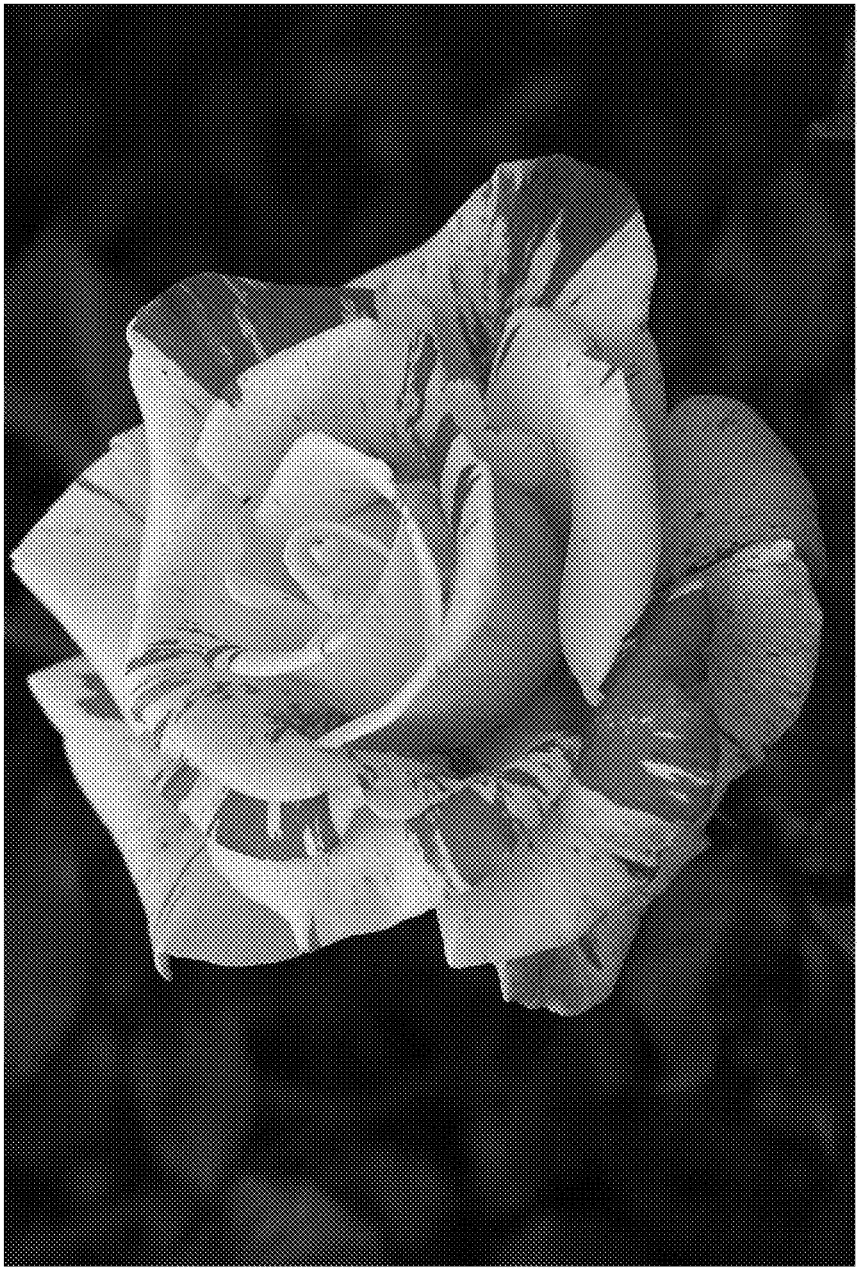

* * * * *